(12) United States Patent
Goff

(10) Patent No.: US 7,997,276 B2
(45) Date of Patent: Aug. 16, 2011

(54) RESPIRATION PILLOW

(76) Inventor: James E. Goff, Terra Ceia, FL (US)

( * ) Notice: Subject to any disclaimer, the term of this patent is extended or adjusted under 35 U.S.C. 154(b) by 275 days.

(21) Appl. No.: 12/471,777

(22) Filed: May 26, 2009

(65) Prior Publication Data

US 2010/0300455 A1 Dec. 2, 2010

(51) Int. Cl.
*A61G 15/00* (2006.01)
*A61F 5/56* (2006.01)
*A47C 20/00* (2006.01)
*F16K 15/00* (2006.01)

(52) U.S. Cl. ............... 128/845; 128/848; 5/636; 5/637; 5/638; 5/644; 137/511

(58) Field of Classification Search ............ 128/845, 128/848; 55/385.1, 420; 5/636, 637, 638, 5/652.1, 652.2, 644; 137/511, 512
See application file for complete search history.

(56) References Cited

U.S. PATENT DOCUMENTS

| | | | |
|---|---|---|---|
| 2,107,962 A | 2/1938 | Sheasby | |
| 3,315,282 A * | 4/1967 | Lowery et al. | 5/638 |
| 4,752,064 A * | 6/1988 | Voss | 5/638 |
| 4,826,479 A | 5/1989 | Burgin et al. | |
| 5,220,699 A * | 6/1993 | Farris | 5/636 |
| 5,960,494 A | 10/1999 | Gilliland et al. | |
| 6,230,350 B1 | 5/2001 | Goldstein | |
| 6,427,272 B1 | 8/2002 | Yacoub | |
| 6,842,924 B1 | 1/2005 | Walters | |
| 6,913,019 B2 | 7/2005 | Johns et al. | |
| 7,063,085 B2 | 6/2006 | Silva et al. | |
| 7,111,445 B2 * | 9/2006 | Threlkeld et al. | 57/229 |
| 2008/0011305 A1 | 1/2008 | Chandran et al. | |
| 2008/0222813 A1 | 9/2008 | Aikman | |

* cited by examiner

*Primary Examiner* — Patricia Bianco
*Assistant Examiner* — George N Phillips
(74) *Attorney, Agent, or Firm* — Anton J. Hopen; Smith & Hopen, P.A.; Ronald E. Smith

(57) ABSTRACT

A device for face-down, prone respiration comprising a head support made of resilient material having a facial cavity conformable to the contours of a person's face, a plenum cavity in fluid communication with the person's face, a substantially L-shaped support base removably engaged to the head support, a horizontal member of the base engaged underneath the head support and a vertical member of the base engaged to an end of the head support proximate to the facial cavity and in fluid communication with the plenum cavity, the vertical member having at least one air pump intake pathway and at least one exhalation discharge pathway integral to the base whereby air pumped through at least one air pump intake pathway creates a plenum in plenum cavity which is inhaled by person and air exhaled by person is discharged back into plenum cavity and out the at least one exhalation discharge pathway.

8 Claims, 8 Drawing Sheets

RESPIRATION PILLOW

BACKGROUND OF THE INVENTION

The present invention relates to a head rest for supporting the head of a user while sleeping and providing a positive air pressure (plenum) environment for respiration.

Continuous Positive Airway Pressure (CPAP) is a method of respiratory ventilation used primarily in the treatment of sleep apnea, for which it was first developed. CPAP ventilation is also commonly used for critically ill patients in hospital with respiratory failure, and in newborn infants (neonates). In these patients, CPAP ventilation can prevent the need for endotracheal intubation, or allow earlier extubation. Sometimes patients with neuromuscular diseases use this variety of ventilation as well. Often people with brain injury need these machines, as well as speech therapy to try to compensate for impaired use of the body, including the airway passages.

The CPAP machine was initially used mainly by patients for the treatment of sleep apnea at home, but now is in widespread use across intensive care units as a form of ventilation. Obstructive sleep apnea occurs when the upper airway becomes narrow as the muscles relax naturally during sleep. This reduces oxygen in the blood and causes arousal from sleep. The CPAP machine stops this phenomenon by delivering a stream of compressed air via a hose to a nasal pillow, nose mask or full-face mask, splinting the airway (keeping it open under air pressure) so that unobstructed breathing becomes possible, reducing and/or preventing apneas and hypopneas. It is the air pressure, and not the movement of the air, that prevents the apneas.

The CPAP machine blows air at a prescribed pressure (also called the titrated pressure). The necessary pressure is usually determined by a sleep physician after review of a study supervised by a sleep technician during an overnight study (polysomnography) in a sleep laboratory. The titrated pressure is the pressure of air at which most (if not all) apneas and hypopneas have been prevented, and it is usually measured in centimetres of water (cm $H_2O$). The pressure required by most patients with sleep apnea ranges between 6 and 14 cm $H_2O$. A typical CPAP machine can deliver pressures between 4 and 20 cm $H_2O$. More specialized units can deliver pressures up to 25 or 30 cm $H_2O$.

CPAP treatment can be highly effective in treatment of obstructive sleep apnea. For some patients, the improvement in the quality of sleep and quality of life due to CPAP treatment will be noticed after a single night's use. Often, the patient's sleep partner also benefits from markedly improved sleep quality, due to the amelioration of the patient's loud snoring. Given that sleep apnea is a chronic health issue, ongoing care is needed to maintain CPAP therapy.

A CPAP system commonly comprises a flow generator (CPAP machine) which provides the airflow, an interface (nasal or full face mask, nasal pillows, or less commonly a lip-seal mouthpiece) which provides the connection to the user's airway, and a hose which connects the flow generator (sometimes via an in-line humidifier) to the interface. Less commonly, CPAP systems may include a humidifier to add moisture to low humidity air. A heated water chamber can also be employed to increase user comfort by eliminating the dryness of the compressed air. The temperature can usually be adjusted or turned off to act as a passive humidifier if desired. In general, a heated humidifier is either integrated into the unit or has a separate power source (i.e. plug).

A ramp may be used to temporarily lower the pressure if the user does not immediately sleep. The pressure gradually rises to the prescribed level over a period of time that can be adjusted by the patient and/or the DME provider. Some devices are equipped with an exhalation pressure relief feature which causes a short drop in pressure during exhalation to reduce the effort required.

Most modern devices include data logging records for basic compliance info or detailed event logging, allowing the sleep physician (or patient) to download and analyze data recorded by the machine to verify treatment effectiveness.

Prospective CPAP candidates are often reluctant to use this therapy, since the nose mask and hose to the machine look uncomfortable and clumsy, and the airflow required for some patients can be vigorous. Some patients will develop nasal congestion while others may experience rhinitis or a runny nose. Some patients adjust to the treatment within a few weeks, others struggle for longer periods, and some discontinue treatment entirely.

CPAP manufacturers frequently offer different models at different price ranges, and CPAP masks have many different sizes and shapes, so that some users need to try several masks before finding a good fit. These different machines may not be comfortable for all users. Where the mask contacts the skin must be free from dirt and excess chemicals (such as skin oils). Shaving before mask-fitting may be necessary. These nuisances, as well as others, also prevent users from sleeping in the prone position.

SUMMARY OF INVENTION

The present invention includes a device for face-down, prone respiration comprising a head support made of resilient material having a facial cavity conformable to the contours of a person's face, a plenum cavity in fluid communication with the person's face, a substantially L-shaped support base removably engaged to the head support, a horizontal member of the base engaged underneath the head support and a vertical member of the base engaged to an end of the head support proximate to the facial cavity and in fluid communication with the plenum cavity, the vertical member having at least one air pump intake pathway and at least one exhalation discharge pathway integral to the base whereby air pumped through at least one air pump intake pathway creates a plenum in plenum cavity which is inhaled by person and air exhaled by person is discharged back into plenum cavity and out the at least one exhalation discharge pathway.

The device may further include a one-way check valve in the vertical member oriented so that a plenum in plenum cavity maintains check valve in a closed state and a vacuum in plenum cavity opens the check valve to permit inhalation in the event the volume of air introduced through air pump intake pathway is insufficient to enable proper respiration. A mechanical barrier secured over the check valve (such as a mushroom cap) inhibits exterior objects from blocking the operation of check valve while permitted accessibility to airflow.

A plurality of head supports are interchangeable with support base. The head supports may be of differing thickness, shape or material construction. However, the base of the head supports are uniform to permit consistent, substantially fluid-tight engagement with the support base.

The support base may be constructed of heat-resistant and/or chemically-resistant material whereby it may removed from head support and disinfected.

As the person may sleep for extended periods of time in a face-down, prone position, a fluid discharge basin is provided on horizontal member and under facial cavity wherein saliva may be collected and removed from device after use.

An advantage of the present invention is that it provides a plenum for face-down, prone respiration.

Another advantage of the present invention is that air intake and exhalation are oriented forward of the person's head thereby allowing the torso and arms to be unencumbered with air supply conduits, power cables or the like. The person may wrap his or her arms around the sides of the device without interference.

Yet another advantage of the present invention is that the same support base is interchangeable with a plurality of different head supports. One individual may prefer softer material versus another individual that may prefer material that is firmer. Another individual may prefer their face elevated higher than another. Yet another individual may seek a wider head support while another individual may require one that is narrower. Furthermore, head supports may need periodic cleaning or replacement which is facilitated by the bifurcation of resilient head support and rigid support base.

Yet another advantage of the present invention is the chemical and/or temperature-resistant construction of the base which enables efficient sanitization. In a hospital setting, the support base may be reusable between patients with the head support replaced between patients. For home users, the support base may be placed into the dishwasher for periodic cleaning. This is a distinct advantage over the prior art as microbial and viral infections occur frequently through respiration. Thus, convenient disinfection of the device constitutes a substantial advancement over the prior art.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

Figure 1:
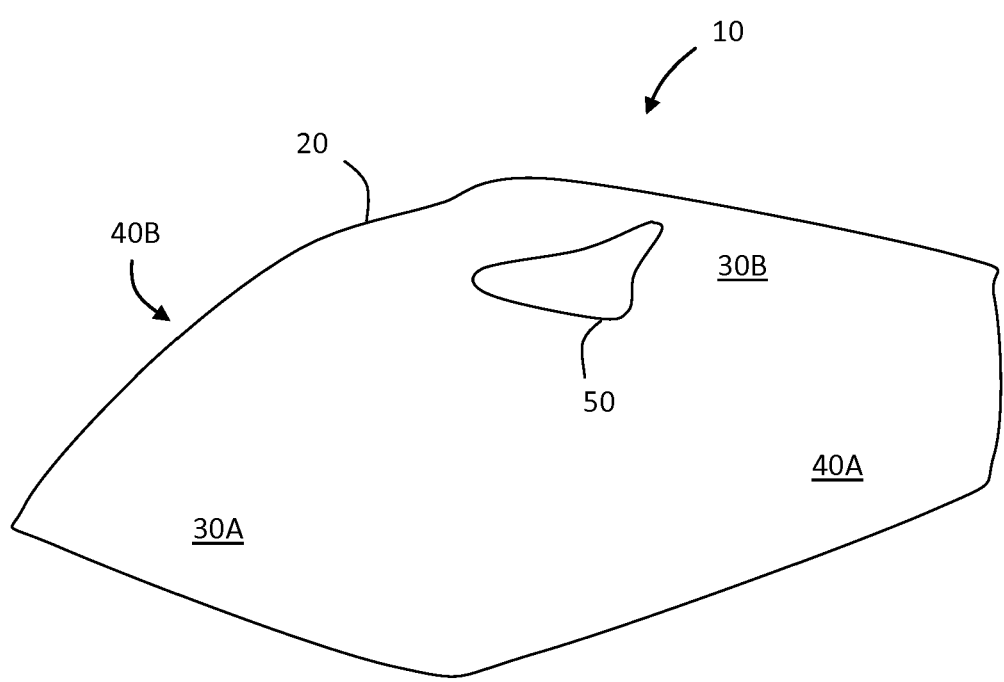
FIG. 1 is an elevated, isometric view of an embodiment of the invention.

Turning to FIG. 1, respiration device is denoted as numeral 10 as a whole. In the embodiment shown, head support 20 is a wedge shaped having lower edge 30A and elevation top 30B. When engaged by a person laying face down, the person's torso rests on lower edge 30A while the head is supported at elevation top 30B. The person's right shoulder and arms (if extended upward) rests over right vertical side 40A. The person's left shoulder and arms (if extended upward) rest over left vertical side 40B. Facial cavity 50 is conforms to the contours of the person's face to at least resist fluid permeability.

Figure 2:
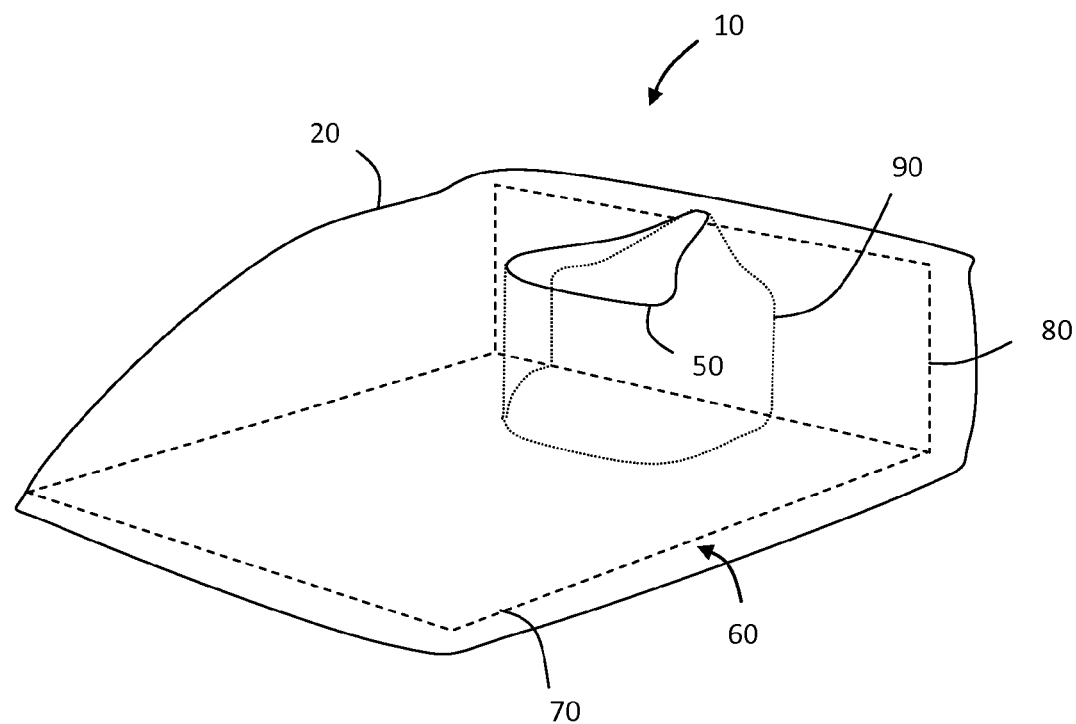
FIG. 2 is an elevated, partially sectional, isometric view of an embodiment of the invention.

In FIG. 2, substantially L-shaped support base 60 engages the bottom and elevation top 30B of head support 20. Support base 60 comprises horizontal member 70 and vertical member 80. Support base 60 is substantially rigid in comparison to resilient and conformable head support 20. Plenum cavity 90 is fluidly coupled to a portion of vertical member 80, a portion of horizontal member 70 and facial cavity 50. Plenum cavity 90 is formed from interstitial space within head support 20.

Figure 3:
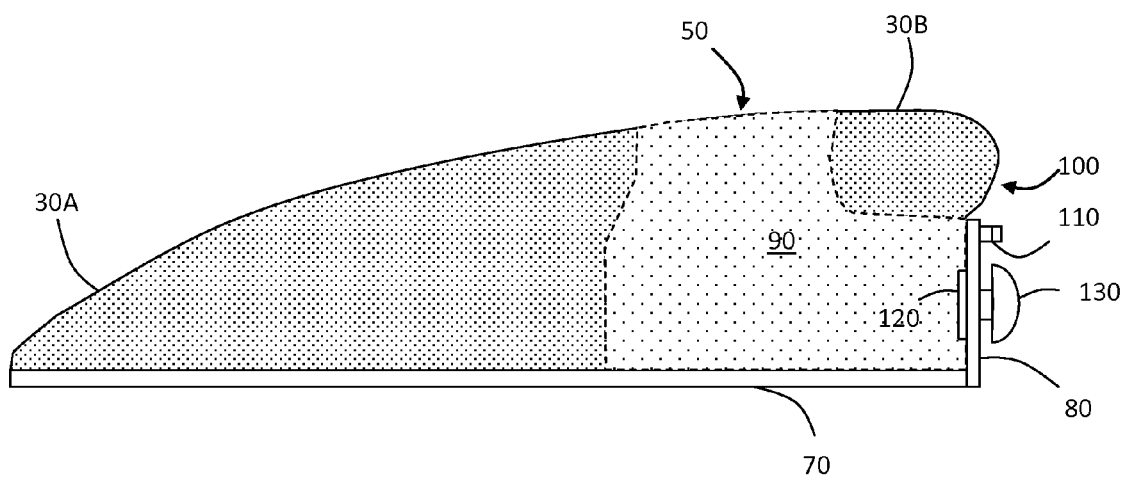
FIG. 3 is an elevated, partially section, side view of an embodiment of the invention.

In FIG. 3, a side view shows head support 20 gaining thickness from lower edge 30A to elevation top 30B. A sectional view shows plenum cavity 90 fluidly coupled to a portion of vertical member 80, a portion of horizontal member 70 and facial cavity 50. Support overhang 100 extends over vertical member 80 so that a person does not accidentally compress head support 20 to press against substantially rigid vertical member 80. Vertical member 80 further comprises air pump intake pathway 110 which is coupled to an air pump (not shown) which introduces air into plenum cavity 90 to assist in respiration. In the unlikely event that a malfunction exists with the air pump, one-way check valve 120 in vertical member 80 is oriented so that a plenum in plenum cavity maintains check valve in a closed state and a vacuum in plenum cavity opens check valve 120 to permit inhalation in the event the volume of air introduced through air pump intake pathway 110 is insufficient to enable proper respiration. Mechanical barrier 130 is secured over the exterior of check valve to inhibit exterior objects (e.g., pillow, sheets, comforter, a wall, a person's arm, etc.) from blocking the operation of check valve. In the illustrated embodiment of the invention mechanical barrier 130 is a mushroom-shaped cover that prevents an obstruction from sealing check valve 120 against proper operation.

Figure 4:
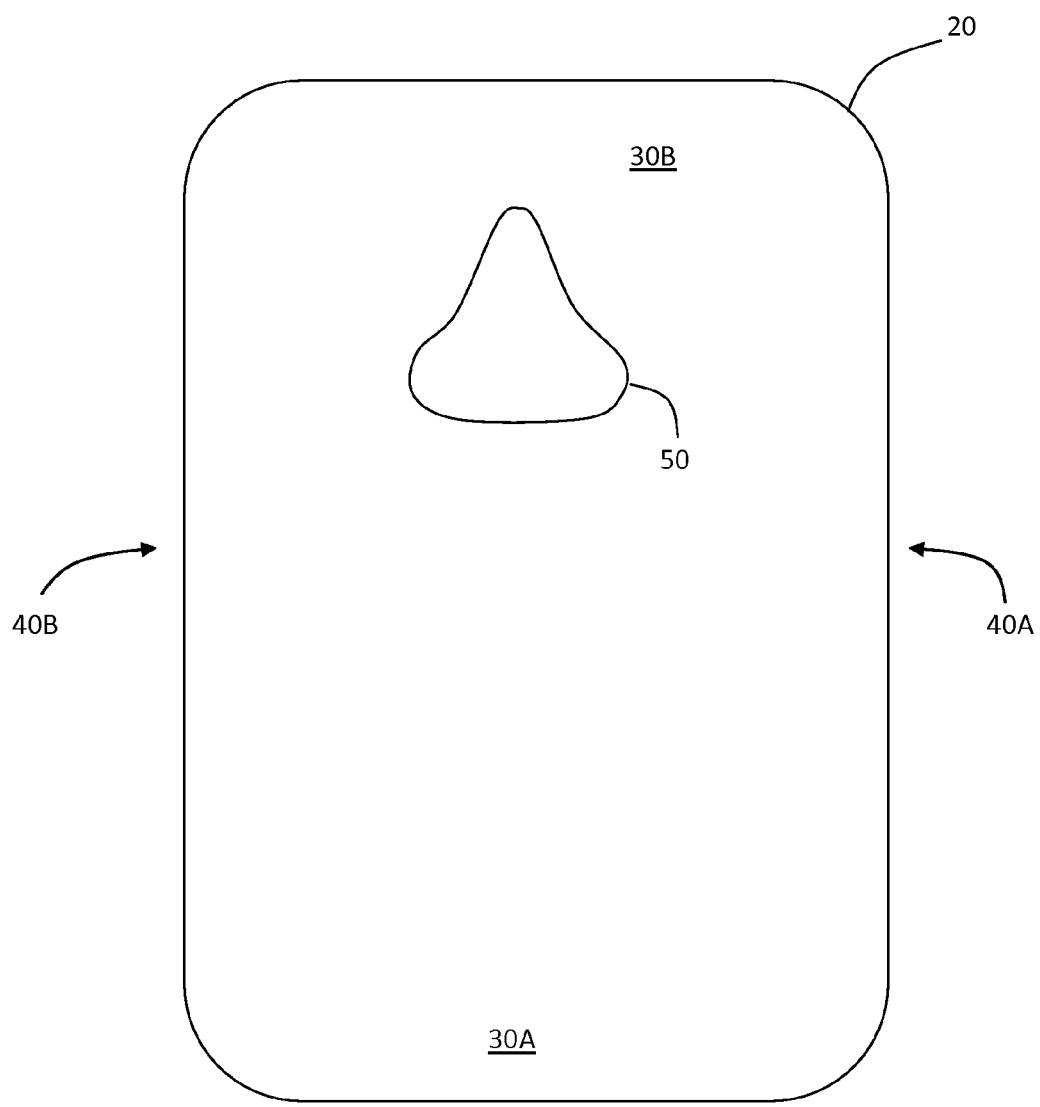
FIG. 4 is an elevated, top-down view of an embodiment of the invention.

In FIG. 4, a top-down view of head support 20 shows lower edge 30A, elevation top 30B, right vertical side 40A and left vertical side 40B. Facial cavity 50 engages the face of the wearer whereby the bridge of the nose is engaged at the upper portion of facial cavity 50 and the person's mouth is engaged at the lower portion of facial cavity 50. An important advantage of this design over prior art masks is that air pumped out of the present invention is discharged away from the ocular area of the person's face. Thus, excessive drying and potential infection of the eyes is reduced.

Figure 5:
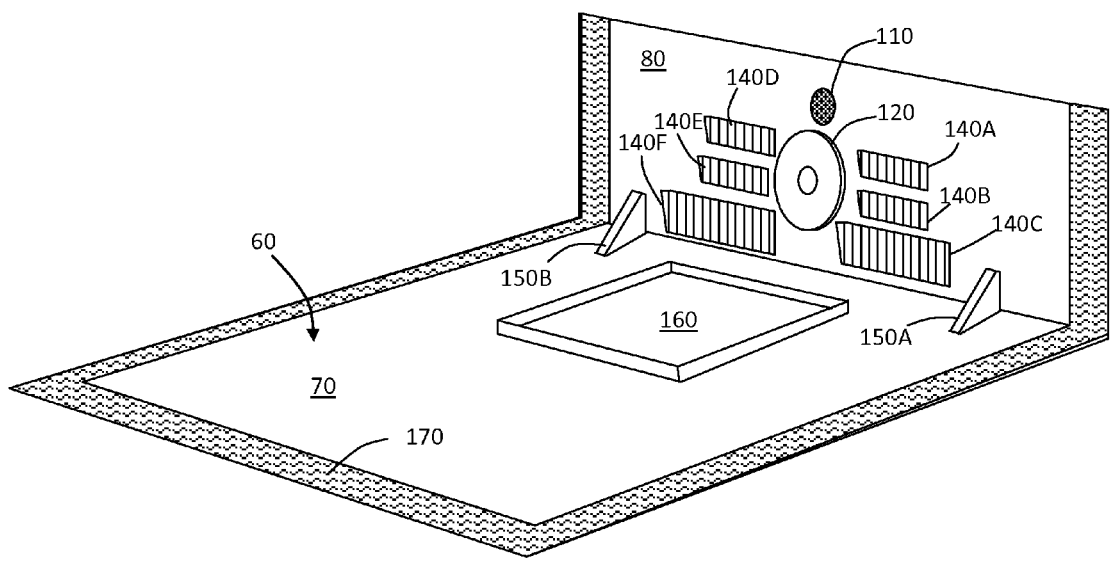
FIG. 5 is an elevated, isometric view of an embodiment of the invention showing the support base.
Figure 6A:
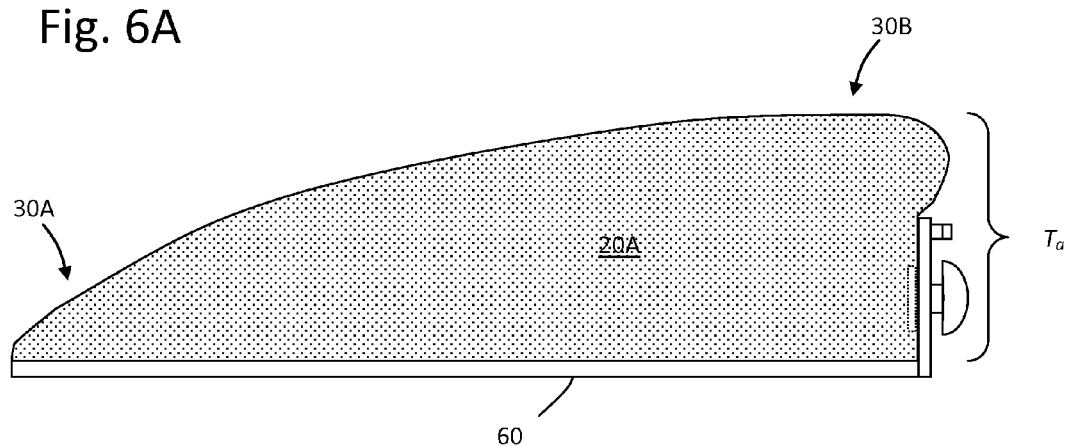
FIGS. 6A-C are elevated, side views of embodiments of the invention showing variable head support thickness.
Figure 6B:
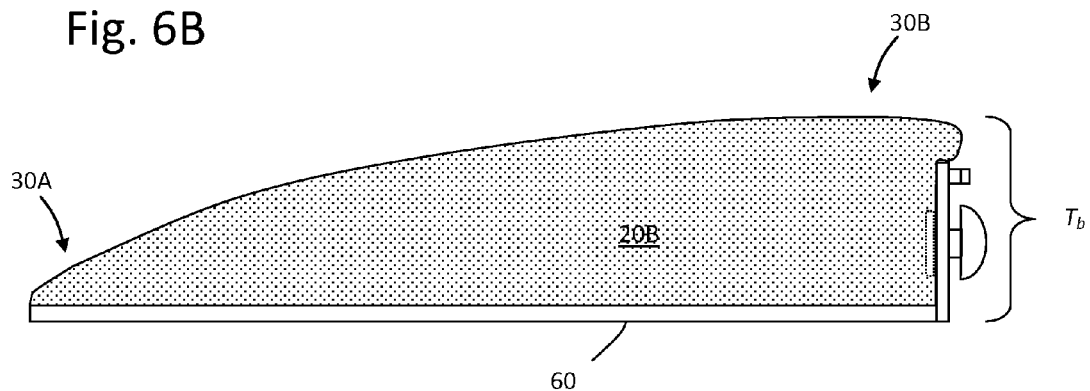
Figure 6C:
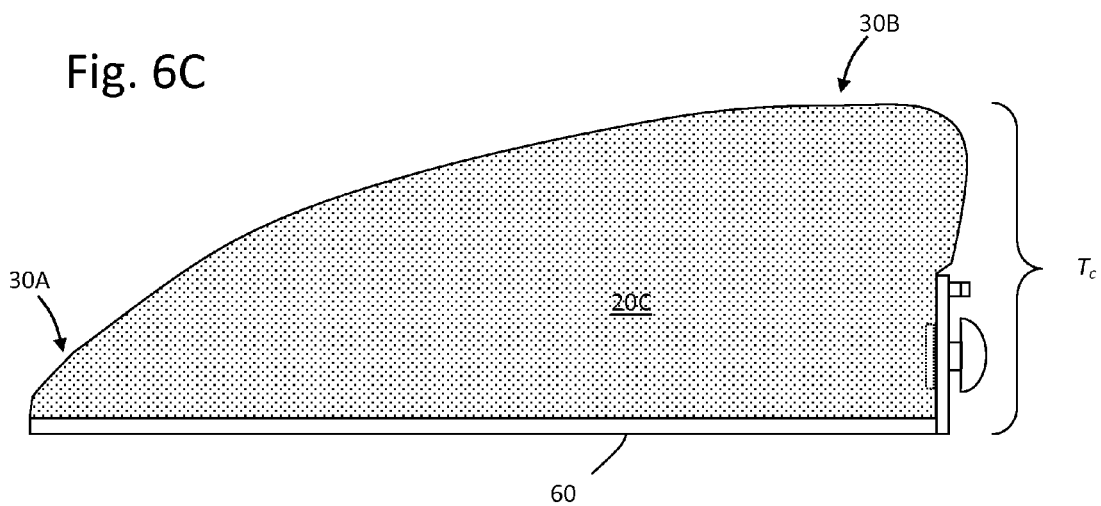

In FIG. 5, head support 20 is removed to better view support base 60. Check valve 120 and air pump intake pathway 110 are provided on vertical member 80. Exhalation discharge pathways 140A-F allow air circulation and the removal of moisture and carbon dioxide. Exhalation discharge pathways 140A-F are sized to permit sufficient back-pressure to maintain a plenum in plenum cavity 90 yet are sufficiently porous to ensure fresh air is circulated for proper respiration. In an embodiment of the invention, exhalation discharge pathways 140A-F are adjustable to permit the increase or decrease in plenum pressure according to the needs of the operator. They may be louvered, sealable or otherwise dampened as needed. Support wedges 150A-B provide enhanced rigidity to support base and fluid discharge basin 160 is positioned under facial cavity 50 to collect saliva and any other liquid discharged from user's oral-nasal passages. Fluid discharge basin 160 may be removable from support base 60 to provide easy cleaning of the device on a regular basis. In the embodiment illustrated head support 20 engages support base 60 by a hook and loop fastener perimeter 170. A simple engagement between head support 20 and support base 60 enables a plurality of head supports 20A-C to interchange with support base 60 as shown in FIGS. 6A-C. In FIGS. 6A-C, head supports 20A-C are elevated from lower edge 30A to elevation top 30B. Elevation top 30B has various thicknesses across head supports 20A-C denoted as $T_a$ through $T_c$. It should be noted this thickness variability is only one example. Material construction, shape, resilience, color, and the like may be varied.

Figure 7:
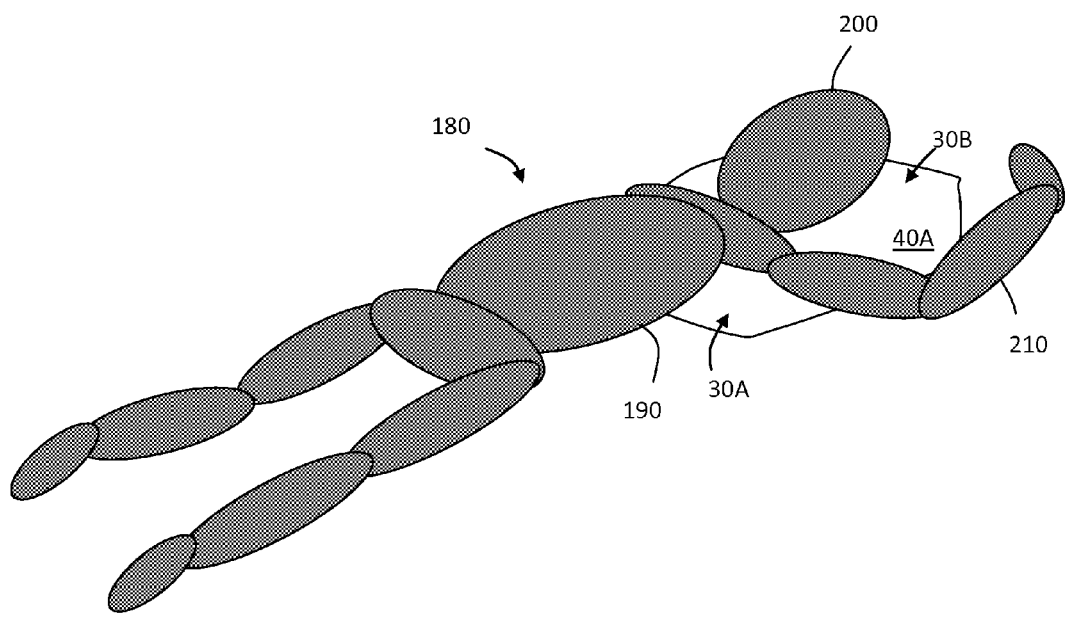
FIG. 7 is an elevated, isometric view of an embodiment of the invention showing a person using the invention.

In FIG. 7, an anthropomorphic representation of person 180 is shown using the present invention in a prone, face down position. Torso 190 lays over lower edge 30A and head 200 engages facial cavity 50 at elevation top 30B. An advantage of the present invention is shown whereby air pumps, exhalation discharge and the like take place away from the person's head, torso and arms 210. Person 180 can wrap his or her arms 210 around vertical sides 40A-B without inhibiting the proper operation of the device. In contradistinction, masks placed over the face and the fluid connection to air pumps and/or electrical connections to power supplies inevitably get tangled in all but the stillest sleepers.

Figure 8:
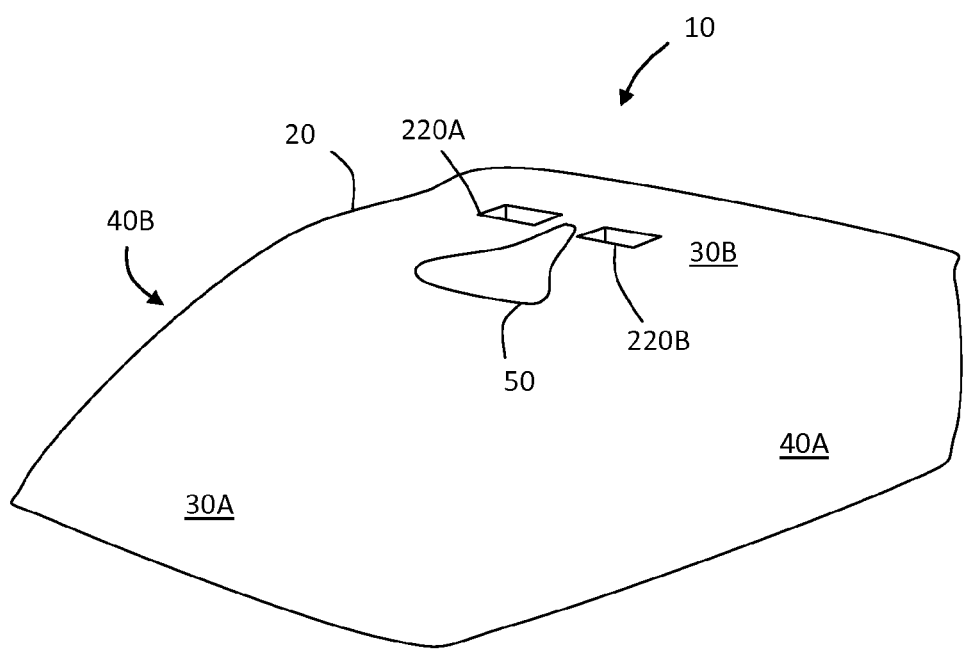
FIG. 8 is an elevated, isometric view of an alternate embodiment of the invention having a plurality of eye cavities.

In FIG. 8, a plurality of eye cavities 220A-B are aligned with the ocular area of the person. Eye cavities 220A-B may provide a more comfortable engagement with head support 20 by avoiding compression between head support 20 and the person's eyes. Eye cavities 220A-B may be of any predetermined geometric configuration and the shapes illustrated are exemplary only. Eye cavities 220A-B may be fluidly coupled to plenum cavity 90 to provide air flow to the ocular area. Alternatively, eye cavities 220A-B may not be fluidly coupled to avoid drying out of the eyes which may result in infection.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. A device for face-down, prone respiration comprising:
    a head support made of resilient material having a facial cavity conformable to the contours of a person's face;
    a plenum cavity in fluid communication with the person's face;
    a substantially L-shaped support base removably engaged to the head support;
    a horizontal member of the base engaged underneath the head support;
    a vertical member of the base engaged to an end of the head support proximate to the facial cavity and in fluid communication with the plenum cavity;
    the vertical member having at least one air pump intake pathway and at least one exhalation discharge pathway integral to the base whereby air pumped through said at least one air pump intake pathway creates a plenum in said plenum cavity which is inhaled by said person and air exhaled by said person is discharged back into said plenum cavity and out the at least one exhalation discharge pathway; and
    a one-way check valve disposed in the vertical member oriented so that a plenum in said plenum cavity maintains said one-way check valve in a closed state and a vacuum in said plenum cavity opens the one-way check valve to permit inhalation in the event the volume of air introduced through said at least one air pump intake pathway is insufficient to enable proper respiration.

2. The device of claim 1, further comprising a mechanical barrier secured over the one-way check valve to inhibit exterior objects from blocking the operation of said one-way check valve.

3. The device of claim 1 wherein each head support of a plurality of head supports is interchangeable with said support base.

4. The device of claim 3 wherein each head support of the plurality of head supports is of differing thickness.

5. The device of claim 1 wherein the support base is constructed of heat-resistant material whereby it may be removed from said head support and disinfected.

6. The device of claim 1 wherein the support base is removably connected to said head support so that it may be removed from said head support and disinfected.

7. The device of claim 1, further comprising a fluid discharge basin on said horizontal member and under said facial cavity wherein saliva may be collected and removed from said device after use.

8. The device of claim 1 further comprising at least one eye cavity in said head support that is proximate to said facial cavity.

* * * * *